United States Patent
Reinstadtler et al.

(10) Patent No.: US 7,360,404 B2
(45) Date of Patent: Apr. 22, 2008

(54) METHOD FOR DETERMINING TRIBOLOGICAL PROPERTIES OF A SAMPLE SURFACE USING A SCANNING MICROSCOPE (SEM) AND ASSOCIATED SCANNING MICROSCOPE

(75) Inventors: Michael Reinstadtler, Sulzbach (DE); Ute Rabe, Saarbrucken (DE); Walter Arnold, Saarbrucken (DE)

(73) Assignee: Fraunhofer-Gesellschaft zur Förderung der Angelwandten Forschung E.V., Munich (DE)

( * ) Notice: Subject to any disclaimer, the term of this patent is extended or adjusted under 35 U.S.C. 154(b) by 164 days.

(21) Appl. No.: 10/524,729

(22) PCT Filed: Aug. 14, 2003

(86) PCT No.: PCT/EP03/09054

§ 371 (c)(1),
(2), (4) Date: Nov. 16, 2005

(87) PCT Pub. No.: WO2004/018963

PCT Pub. Date: Mar. 4, 2004

(65) Prior Publication Data

US 2006/0150719 A1    Jul. 13, 2006

(30) Foreign Application Priority Data

Aug. 16, 2002  (DE) ............................. 102 37 627

(51) Int. Cl.
*G01B 5/28* (2006.01)
*G01N 13/16* (2006.01)
(52) U.S. Cl. ........................................... 73/105
(58) Field of Classification Search .................. 73/105
See application file for complete search history.

(56) References Cited

U.S. PATENT DOCUMENTS 5,804,708 A    9/1998    Yamanaka et al.

(Continued)

FOREIGN PATENT DOCUMENTS

DE    43 24 983 C2    7/1996

(Continued)

OTHER PUBLICATIONS

Arnold, W. et al.; "Atomic Force Microscopy at Ultrasonic Frequencies", Proceeding International Conference on Non-Destructive Evaluation and Reliability of Mircro- and Nanomaterial Systems; International Society for Optical Engineering, SPIE, vol. 4703, 2002, pp. 53-64.*

(Continued)

*Primary Examiner*—Daniel S. Larkin
(74) *Attorney, Agent, or Firm*—Antonelli, Terry, Stout & Kraus, LLP.

(57) ABSTRACT

A method for examining a surface of a sample is described using an atomic force scanning microscope (AFM) comprising a cantilever with a longitudinal extension along which a measuring tip is disposed, which is selectively arranged relative to the sample surface by a means for driving and whose spatial position is detected using a sensor unit. Vibration excitation is conducted at excitation amplitudes which produce inside the cantilever torsional amplitudes with maximum values which form a largely (substantively) constant plateau value despite increasing excitation amplitudes and the resonance spectra, in a range of maximum values of the torsional amplitudes, a widening of the resonance spectrum which is determinable by a plateau width. The resonance spectra, preferably the plateau value, the plateau width and/or the gradient of the respective resonance spectra are used for examining the sample.

18 Claims, 1 Drawing Sheet

U.S. PATENT DOCUMENTS 5,852,233 A * 12/1998 Arnold et al. ................. 73/105
6,880,386 B1 * 4/2005 Krotil et al. ................... 73/105

FOREIGN PATENT DOCUMENTS

DE 199 00 114 A1 8/2000

OTHER PUBLICATIONS

Rabe, U. et al.; "Quantitative Determination of Contact Stiffness Using Atomic Force Acoustic Microscopy", Ultrasonics, vol. 38, 2000, pp. 430-437.*

Yamanaka, K. et al.; "Quantitative Material Characterization by Ultrasonic AFM", Surface and Interface Analysis, vol. 27, 1999, pp. 600-606.*

Rabe, U. et al.; "Probing Linear and Non-linear Tip-Sample Interaction Forces by Atomic Force Acoustic Microscopy", Surface and Interface Analysis, vol. 27, 1999, pp. 386-391.*

Rabe, U. et al.; "Evaluation of the Contact Resonance Frequencies in Atomic Force Microscopy as a Method for Surface Characterisation (Invited)", Ultrasonics, vol. 40, 2002, pp. 49-54.*

* cited by examiner

METHOD FOR DETERMINING TRIBOLOGICAL PROPERTIES OF A SAMPLE SURFACE USING A SCANNING MICROSCOPE (SEM) AND ASSOCIATED SCANNING MICROSCOPE

BACKGROUND OF THE INVENTION

1. Field of the Invention

The present invention relates to a method for examining a sample surface using an atomic force scanning microscope comprising a cantilever with a longitudinal extension, along which the measuring tip is arranged precisely relative to a sample surface by means of a means for driving, the spatial position of the measuring tip being determined by a sensor unit. The microscope is further provided with at least one ultrasound generator with which vibration excitation is initiated at a given excitation frequency between the sample surface and the cantilever. The measuring tip of the cantilever is brought into contact with the sample surface in such a manner that the oscillations imparted to the measuring tip are oriented lateral to the sample surface and perpendicular to the length of the cantilever. The torsional vibrations induced in the cantilever are detected and analyzed by means of an evaluation unit.

2. Description of the Prior Art

The development of an atomic force scanning microscope has permitted major achievements in the field of examination of surface properties, in particular in the characterization of surface properties. For the first time, it is possible to obtain information concerning surfaces and areas close to the surface of very different samples in nanometer resolution even in the magnitude of single atoms. Friction force microscopy, a further development of the atomic force scanning microscope, permitted for the first time studying one of the oldest problems in science, the examination of friction, on this scale.

DE 43 24 983 C2 describes an acoustical microscope operating on the technological basis of an atomic force scanning microscope that is able to measure the topography as well as the elastic properties of the surface of a sample. The microscope comprises a cantilever designed as a leaf spring, usually with a length of between 100 μm and 500 μm, attached to the one end of which is a pyramid-shaped measuring tip having a tip radius of curvature of about 50 nanometers.

In order to measure and examine the sample surface holistically, the cantilever and the measuring tip attached thereto are scanned over the sample surface with the aid of a suitable means for moving in such a manner that the measuring tip makes contact with the sample surface with a given vertical load at every single scanning point. The optical sensor unit permits determining the degree of deformation of the cantilever and thus the topography-based excursion of the measuring tip. Usually, the optical sensor unit is provided with a laser diode from which a laser beam directed at the cantilever is emitted, reflected thereat, and detected by a position-sensitive photodiode. During scanning, the cantilever and the measuring tip are guided perpendicular to the sample surface via a regulation loop in such an active manner that the excursion of the cantilever, and the vertical load with which the cantilever lies on the sample surface via the measuring tip, remains constant. The regulation tension required for the excursion is usually converted into a distance value and is correspondingly depicted as an encoded color value in a representation showing the surface topography.

In order to also be able to determine the elastic properties of the surface sample, an ultrasound generator is provided which induces oscillations in the surface sample while the measuring tip lies at a scanning point of the sample surface. Vibration excitation by coupling in ultrasonic waves leads to normal vibrations of the sample surface which induce high-frequency oscillating bending vibrations in the cantilever along its longitudinal extension.

Detection by the ultrasonically induced, high-frequency vibration behavior of the cantilever permits obtaining information about the elastic properties of the sample surface. The problem with this measuring situation that needs to be resolved lies in the decoupling due to the measurement of the superimposed excursions of the cantilever, which result, on the one hand, from the topography measurement due to which the vertical load with which the measuring tip lies on the sample surface remains, as constant as possible and, on the other hand, which cause the ultrasonically induced normal vibrations of the sample surface transmitted to the cantilever via the measuring tip.

In order to obtain a reliable measuring signal with a high as possible signal/noise ratio for measuring the elasticity, the ultrasonically induced vibration excitation of the sample surface occurs at frequencies which are at least one magnitude greater than the resonant frequency of the cantilever having the measuring tip attached thereto. Using two photodiodes with different temporal responding behavior, on which the light beam reflected at the cantilever impinges, permits selective detection and evaluation of the vibration behavior of the cantilever. Thus, the photodiode with a slow response behavior is able to solely detect the excursions resulting from the contour-based readjustment of the cantilever for determining the topography. On the other hand, the second photodiode, which has a bandwidth window in the MHz range, is provided for determining the high-frequency vibration parts of the cantilever. Especially suited therefor are, for example, single-cell light-sensitive detectors with a smooth-edged means for shading, for example in the form of a razor blade or a so-called heterodyne running-time interferometer, in the one interferometer arm of which a frequency shift means is provided. Such a rapid type responding detection unit can also be designed based on a capacity measurement, in which the measuring capacity is formed from the cantilever and a needle-shaped counter-electrode disposed opposite thereto. Further details can be found in the aforementioned printed publication DE 43 24 983 C2.

Contrary to the aforedescribed resonance measurement with vertical modulation, that is the to-be-examined sample surface is excited to normal vibrations U.S. Pat. No. 5,804,708 describes an atomic force microscope with a similar setup, but vibration excitation of the to-be-examined sample occurs with the aid of a signal generator in such a manner that the sample surface imparts vibrations oriented lateral to the sample surface and, in particular, directed transverse in relation to the longitudinal extension of the cantilever.

The vibration excitation directed transverse to the longitudinal extension of the cantilever induces torsional vibrations in the cantilever in contact with the sample surface via the measuring tip, with the measuring tip, which is at least sometimes in contact with the sample surface, executing oscillations which are directed in longitudinal direction to the sample surface and transverse to the longitudinal extension of the cantilever, respectively are polarized. The measuring tip briefly adheres to the sample surface at the point of reversal of the oscillations. The sample surface is deformed by the shear forces acting laterally to the sample surface until, due to friction, the measuring tip slips out of the described state back over the sample surface.

The shear deformations formed at the returning points in dependence on the vertical load with which the measuring tip lies on the sample surface influence the vibration behavior of the measuring tip and consequently that of the cantilever in a manner which characterizes the elastic properties of the sample surface. Thus, it is possible to obtain information about the elastic properties of the sample surface from the vibration behavior, for example from the vibration amplitude and/or the phase of the oscillations occurring in the form of torsional vibrations along the cantilever.

The oscillations initiated by the signal generator in the sample have frequencies of approximately 1 kHz. However, with this measuring method, local resolution has proven unsatisfactory. Only measurements with a local resolution of approximately 100 nm can be achieved. Moreover, the measuring quality achievable with this method permits obtaining only qualitative information about the frictional properties of the sample surface.

SUMMARY OF THE INVENTION

The present invention is a method for examining a surface sample using an atomic force scanning microscope of the aforedescribed manner, in which vibrations are induced in the surface sample, the vibrations being directed lateral to the sample surface and, moreover, being oriented perpendicular to the longitudinal extension of the cantilever, in such a manner that it is possible to obtain qualitative and quantitative information about the frictional properties of the sample surface. In particular, method permits high locally resolved determination of the tribological, that is frictional properties of the sample surface, by means of superimposing a topography measurement, permitting in this manner finely as possibly resolved sample surface mapping with a local resolution of less than 100 nm, preferably less than 10 nm.

A key element of the present invention is that a method for examining a sample surface by means of an atomic force scanning microscope comprising a cantilever with a longitudinal extension, along which a measuring tip is disposed, which is selectively arranged relative to the sample surface via a means for driving and the spatial position of which is detected by a sensor unit, and is provided with at least one ultrasound generator, which initiates a vibration excitation with a given excitation frequency between the sample surface and the cantilever. The measuring tip of the cantilever is brought into contact with the sample surface, in such a manner that the vibrations imparted to the measuring tip are oriented lateral to the sample surface and perpendicular to the longitudinal extension of the cantilever. Torsional vibrations that are formed in the cantilever are detected and analyzed by means of an evaluation unit. Vibration excitation occurs in such a manner that the oscillations executed by the measuring tip have higher harmonic vibration parts relative to the excitation frequency. The vibration excitation preferably occurs with a continuous wave signal which is wobbled, that is varied, within a given excitation frequency range. The excitation frequency range is selected in such a manner that the resonant basic vibration of the cantilever having the measuring tip in contact on the sample surface lies inside the excitation frequency range.

In addition to the selection of a suitable frequency, vibration excitation of the cantilever lying on the sample surface occurs with excitation amplitudes causing in the cantilever torsional vibrations with torsional amplitudes whose torsional amplitude maximum values assume a largely constant plateau value despite increasing excitation amplitudes and whose resonance spectra undergo in the range of the torsional amplitude maximum value a widening of the resonance spectrum which is determinable by the width of the plateau. Finally, the resonance spectra, preferably the plateau value, the plateau width, the gradient of the respective resonance spectra at the flanks of the resonance curve and/or the gradient of the plateau can be utilized to examine the sample surface.

With the aid of the method of the invention, tribological properties, thus for example, the frictional forces or the frictional coefficients acting between the measuring tip and the sample surface, are detected at the sample surface with a local resolution of up to 1 nm. Compared to prior art methods, which at best permit local resolution of approximately 100 nm, the method of the invention is a highly sensitive and most finely suited to a resolving tribological method of analysis. In addition to determining tribological properties at a sample surface, the method of the invention, of course, also permits determination of the topography by adjusting a constant vertical load which the measuring tip of the cantilever lies on the to-be-examined sample surface. With the aid of a means for detecting, low-frequency excursions of the measuring tip are detected via the reflection of light at the cantilever and correspondingly evaluated. The detection signal obtained with the means for detecting representing the low-frequency topography-based excursion of the measuring tip serves, on the one hand, to determine the topography and, on the other hand, as a regulation value, with which the distance between the measuring tip and the sample surface, and the vertical load with which the measuring tip lies on the sample surface is held constant and temporally averaged. In this manner, the method of the invention permits rendering in successive scanning of the surface an accurate microscopic topographic image of the sample surface in a scale of up to 1 nm, the image being able at the same time to provide tribological information about the sample surface.

Measurement of tribological surface properties at a point of the sample surface preferably occurs in several steps. First, for determining the basic resonant frequency of the cantilever in contact with the sample surface via the measuring tip, the ultrasound generator generates vibrations in the form of continuous wave signals whose frequencies are wobbled, that is varied, in a given frequency range. The given frequency comprises preferably frequencies below the basic resonant frequency range of the cantilever in contact with the sample surface via the measuring tip up to thirty times this contact resonant frequency. Typically, frequency wobbling of the excitation frequency occurs in 1 kHz frequency steps within a frequency range between 50 kHz and 10 MHz. For example, in the case of a typical cantilever with a length of 450 μm, there were four torsional resonances in the frequency range between 50 kHz and 3 MHz.

In order to determine the properties of the sample surface, in particular with regard to the tribological properties, such as frictional coefficients etc., the sample is impinged via the ultrasound generator with excitation frequencies lying in the contact resonant frequency $f_r$. Preferably, the excitation frequency range comprises $\Delta f_a$ frequencies from $f_r - \frac{1}{2} f_r$ to $f_r + \frac{1}{2} f_r$. In a particularly advantageous manner, the excitation frequency range $\Delta f_a$ comprises frequencies between $f_r - \frac{1}{2} \Delta f_r$ to $f_r + \frac{1}{2} \Delta f_r$, with $\Delta f_r$ corresponding to the half-width value of the determined resonance curve measured at $f_r$.

Vibration excitation occurs within the framework of a frequency sweep, that is the excitation frequency is wobbled, and varied, in the given excitation frequency range $\Delta f_a$ in the form of single continuous wave signals.

In addition to selecting the excitation frequency range in the range of the contact resonant frequency, of utmost importance is the exact setting of the direction of the vibrations, respectively of the polarization of the vibration of the transverse vibrations induced laterally in the sample surface relative to the longitudinal extension of the cantilever. Setting the measuring tip lying on the sample surface with a defined vertical load results in high-frequency oscillating transverse vibrations transverse to the longitudinal extension of the cantilever which due to the great rise in resonant vibrations constantly "jumps back and forth" between the following three states: 1) the measuring tip rubs over the sample surface; 2) oscillation movement comes to a standstill; 3) the measuring tip moves within an elastic potential, that is the measuring tip briefly engages in a frictional bond with the sample surface, locally deforming the sample surface due to the shear forces directed lateral thereto.

In contrast to the non-resonant case, as described in U.S. Pat. No. 5,804,708, in which the measuring tip executes strict cyclical oscillations with the measuring tip, in the resonant vibration case, the measuring tip dances at least sectionwise chaotically over the sample surface and assumes the aforedescribed states stochastically. This is referred to as "stick-slip" motion. This motion represents a highly dynamic motion behavior.

Due to the measuring situation described above, it is not difficult to understand that the vibration behavior forming inside the cantilever is determined by the tribological contact properties between the measuring tip and the sample surface. If the sample surface is excited, as mentioned in the preceding, with a contact resonant frequency, preferably the basic resonant frequency of the cantilever in contact with the sample surface via the measuring tip to vibrations by means of the ultrasound generator, at low excitation amplitudes, resonant vibration behavior of the cantilever sets in, the resonance curve of which is largely symmetrical. The resonant vibration behavior of the cantilever is detected in a prior art manner by means of an optical sensor unit and is represented in the form of a resonance curve. If the excitation amplitude is raised by successively increasing the excitation voltage with which the ultrasonic wave generator is operated, the recorded resonance spectrum shows deviations from the originally symmetrical resonance curve of such a manner that, despite increasing excitation amplitude, the amplitude of the resonance spectrum assumes a type of saturation value and remains practically constant. Similarly, the form of the resonance curve changes in such a manner that a widening is generated in the upper amplitude range or the resonance curve. Along with the widening of the resonance spectrum of the resonance curve, a sort of plateau forms, whose position remains largely constant despite rising excitation amplitudes, the width of which however also increases with rising excitation amplitudes. According to the invention, it is these characteristic deviations from the symmetric formation of the resonance curve formed by the increase in excitation amplitude that are selectively used to obtain tribological information. This particularly applies to the plateau values, the plateau width, the gradient of the respective resonance spectra at the flanks of the resonance curve and/or the gradient of the plateau yielded by a widening of the resonance spectrum.

The aforedescribed resonant excitation can, of course, also be carried out at contact resonant frequencies of a higher order. Thus, the aforedescribed deviations from the symmetric formation of the resonance curve can be observed not only at the basic resonant frequency, that is in the occurrence of the first torsion mode, but also at higher modes. The widening occurring in the resonance curve at higher modes, such as in the plateau width, can also be utilized for determining the frictional force.

In addition, "overtones" to the excitation frequency can be detected in the resonant behavior of the cantilever as soon as the described flattening at the resonance maximum sets in. Such type overtones can also be detected at higher vibration modes, which also can be utilized to determine the frictional force. For example, if a cantilever in contact with the surface has the first torsion mode at an excitation frequency of 100 kHz, the higher torsion modes lie at 300 kHz, 500 kHz, 700 kHz, etc. The $n^{th}$ torsion mode, therefore, lies at $(2n-1) \times 100$ kHz. If the first torsion mode is excited with a sufficiently high excitation amplitude so that, for example, a flattened torsion peak is visible in the excitation frequency spectrum between 80 kHz and 120 kHz, peaks occur as well at 200 kHz, 300 kHz, 400 kHz, etc., also at frequencies $k \times 100$ kHz, which are singly detectable. The overtones of the excitation frequency that coincide with higher torsion modes (300 kHz, 500 kHz, 700 kHz, . . . ) are, of course, more intensive than the others (200 kHz, 400 kHz, 600 kHz, . . . ).

For detection of the resonant torsional vibrations forming inside the cantilever, at least one temporally high-resolving photodiode is used, whose temporal resolution capacity permits detection of the vibration occurrences with frequencies, which preferably correspond to up to twenty-five times, preferably double to ten times the excitation frequency.

By means of the sequential scanning in the measuring tip along the sample surface, measurements are conducted successively at closely adjacent contact points spaced laterally at least approximately 1 nm under the aforedescribed resonance conditions. On the one hand, the measurements yield information about the surface topography as well as, on the other hand, about the tribological properties at the point of contact. In addition to the topographically determined surface contour, the aforementioned properties of the resonance curve of the cantilever at each point of the to-be-measured sample surface can be plotted and encoded as a color value for representation. For example, changing frictional properties at the sample surface influence the resonant vibration behavior of the cantilever and therefore the vibration amplitude at constant excitation frequency making even the smallest changes in friction detectable as it is these smallest changes in friction that have very sensitive influence on the amplitude behavior, as is clearly indicated by the recorded resonance curves.

For example, the smallest shifting of the flanks of the resonance curve in relation to the frequency axis (x-axis) results in major changes in the resonance amplitude (y-axis). As already mentioned, besides detecting the resonant behavior of the basic vibration of the cantilever, higher harmonic resonances can also be detected and examined and correspondingly encoded as a color value for representation.

BRIEF DESCRIPTION OF THE DRAWINGS

The present invention is made more apparent in the following using preferred embodiments with reference to the accompanying drawings, by way of example, without intention of limiting the scope or spirit of the invention.

DETAILED DESCRIPTION OF THE PREFERRED EMBODIMENTS

Figure 1:
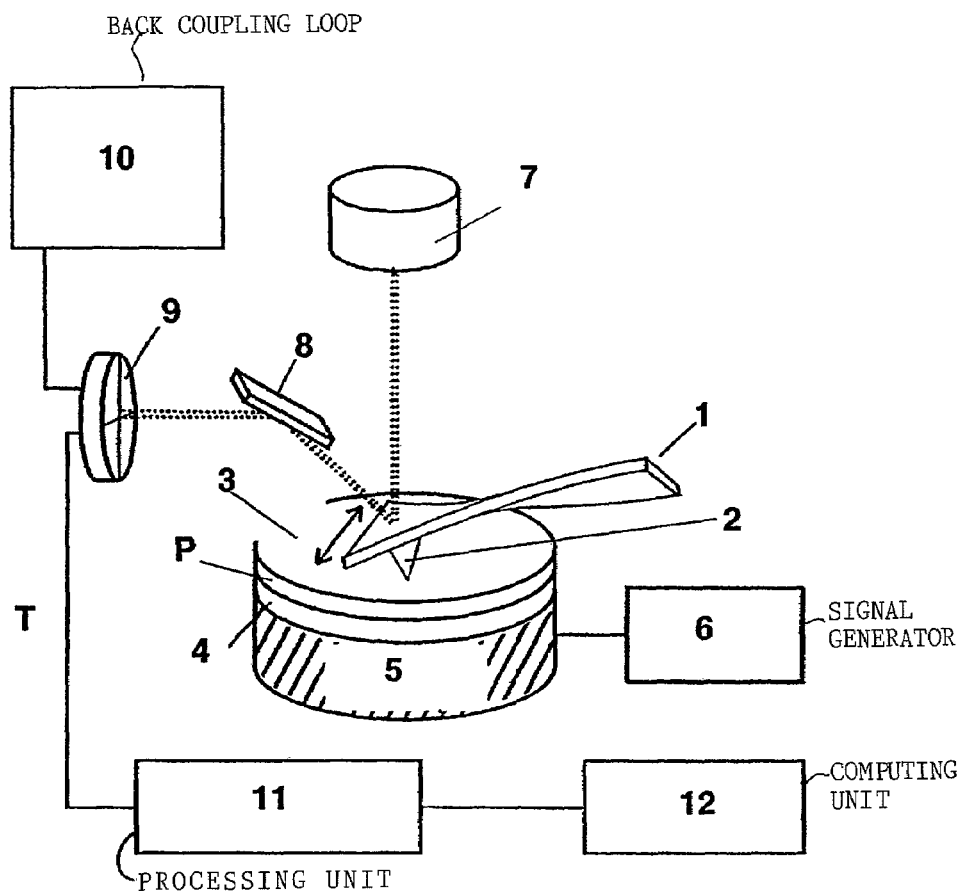
FIG. 1 shows a schematic representation of components for conducting the invented method.

FIG. 1 shows an atomic force scanning microscope for conducting the method of the invention for examining a sample surface, in particular for determining tribological properties on the sample surface. The microscope depicted in FIG. 1 is provided with a cantilever 1, whose measuring tip 2 lies on the sample surface 3 of a sample P. Sample P is in contact with an ultrasonic transducer 5 via a pre-run track or pre-run layer 4. The ultrasonic transducer 5 is set into oscillations by a corresponding signal generator 6. The pre-run layer 4 is, for example, connected on both sides to the sample P and the ultrasonic transducer via a honeycomb layer as an acoustic coupling layer.

An optical sensor unit comprising a laser diode 7, a deflection mirror 8 and a photodiode unit 9, is provided for measuring the vibrations conveyed into the cantilever 1 via the measuring tip 2. The photodiode unit 9 serves, on the one hand, to detect the topographically based, low-frequency excursions of the measuring tip 2 and therewith of the cantilever and, for this reason, is connected to an AFM back-coupling loop 10, which serves to constantly adjust the vertical load with which the measuring tip 2 lies on the sample surface 3. Details concerning such a type control loop are described in the printed publication DE 43 24 983 C2 described in the introductory part hereof.

Similarly, the photodiode unit 9 is able to detect high-frequency vibration parts which are conveyed as a torsional signal T to a computing unit 12 which may perform spectral analysis via a rapid signal processing unit 11 which may be associated with a wideband amplifier, stored, evaluated and finally graphically represented as frictional properties.

For reason of clarity, the friction microscope setup shown quite schematically in FIG. 1 does not show the means for driving required for the spatial arrangement of the cantilever relative to the sample surface, usually provided as a piezo driver means. As it is a state-of-the-art means for driving, here too reference is made to DE 43 24 983 C2.

In order to carry out the examination on sample P according to the present invention, the object of which is measuring the tribological properties at sample surface 3, the ultrasonic transducer 5 is designed and operated in such manner that sample P is set in vibrations solely lateral to the sample surface 3. The vibrations are, in addition, oriented perpendicular to the longitudinal extension of the cantilever 1, respectively are polarized (see arrow in FIG. 1). The mechanical coupling sets the cantilever 1 in contact with the sample surface 3 via the measuring tip 2 in torsional vibrations, which upon reaching a basic resonant frequency lead to a great rise in torsional resonance vibration. For selective determination of the basic resonant frequency $f_r$ of the cantilever 1 in contact with the sample surface 3 via the measuring tip 2, the ultrasound generator 5, which is composed of the vibration generator 6 and the ultrasonic transducer 5, generates a multiplicity of continuous wave signals separated in temporal succession, whose excitation frequencies are wobbled in a given frequency range, including frequencies below the basic resonant frequency of the cantilever up to thirty times this frequency, thereby ensuring that cantilever 1 is excited to torsional vibrations not only with its basic vibration but also begins vibrating at higher mode torsional resonances. Upon reaching a contact resonant frequency, either the basic resonant frequency or a higher harmonic resonant frequency, the excitation amplitude, with which the ultrasonic transducer 5 vibrates, is set in such a manner that measuring tip 2 rubs on the sample surface 3, thus always changing the elastic contact to the sample surface. In detail, at these excitation amplitudes, the measuring tip 2 carries out oscillating sliding movements which are briefly interrupted at the point of reversal of the oscillation by friction bonding between the measuring tip 2 and the sample surface 3.

Figure 2:
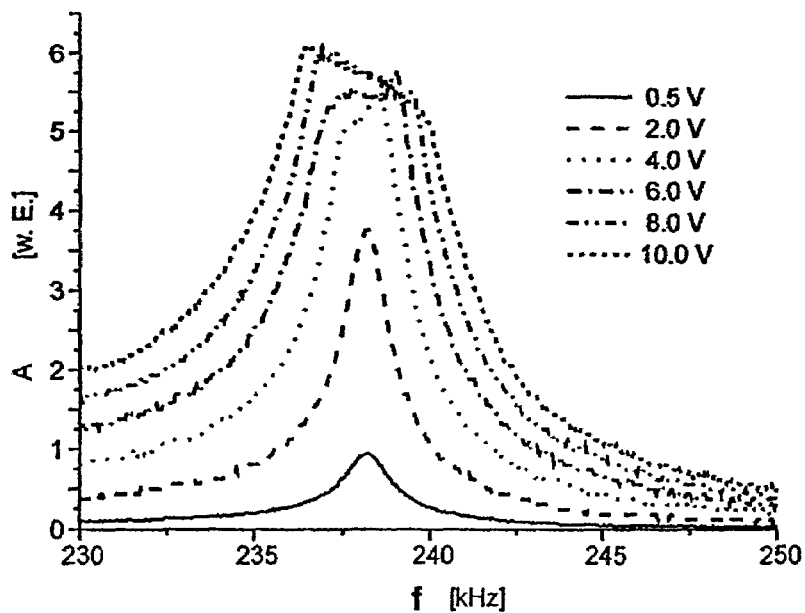
FIG. 2 shows a diagrammatic representation with resonance curves at different excitation amplitudes.

The resonance behavior of the cantilever 1 setting in with this vibration behavior, also described as "stick-slip" vibration behavior, is detected by an optical sensor unit 9 and analyzed more exactly by way of a resonance curve representation. A family of curves obtained with the aid of the measuring setup described in FIG. 1 is depicted in a diagram shown in FIG. 2, which provides an abscissa formed as a frequency axis and an ordinate formed as an amplitude axis. The resonance curves depicted with the different sorts of lines represent the resonance behavior of the cantilever at different excitation amplitudes, and excitation voltages. It appears that at low vibration amplitudes of the ultrasonic transducer, the amplitudes of the respective resonance maximum values increase linearly with the amplitude of the excitation vibration. At excitation voltages of approximately up to 3 to 4V, largely symmetrical resonance curves form. From a certain excitation amplitude, and excitation voltage, the amplitudes of the resonance curves, respectively of the torsion resonances, remain largely constant despite rising excitation voltages, but rather the shape of the resonance curve changes. The reason for such type nonlinear changes in the shape of the resonance curve is found in the afore-described "stick-slip" behavior. If however the excitation amplitude is raised nonetheless, the diagram shows that the position of the torsional resonance remains largely the same and a widening of the spectrum in the form of a plateau occurs in the range of the torsional maximum. It is these curve-changing characteristics that are utilized according to the present invention to determine the frictional properties, and the tribological properties, of the sample surface. This relates, in particular, to the plateau value of the resonance amplitudes, the plateau widths and the gradient of the resonance curve flanks forming a saturation value.

The evaluation of the resonant torsional vibration behavior of the cantilever occurs by means of recording the phase distribution and frequency distribution of the torsional vibrations of the cantilever by way of optical determination of vibrations including using a lock-in amplifier. An alternative to the lock-in amplifier is using a wideband amplifier in conjunction with discrete signal processing for spectral analyses, such as for example the discrete Fourier transformation (DFT), the rapid Fourier transformation (FFT), the wavelet transformations, or the so-called Walsh transformation. Analog spectral analysis is also feasible.

LIST OF REFERENCE cantilever
measuring tip
sample surface
pre-run layer
ultrasonic transducer
signal generator
laser diode
deflection mirror
photodiode unit
AFM back coupling loop
rapid signal processing unit
computing unit
sample
torsional signal excitation frequency
amplitude

What is claimed is:

1. A method for examining a sample surface using an atomic force scanning microscope comprising a cantilever with a longitudinal extension along which a measuring tip is disposed, which is located relative to said sample surface by a means for driving and having a spatial position detected with a sensor, and at least one ultrasound generator, which initiates vibration excitation at an excitation frequency between said sample surface and said cantilever, the measuring tip being brought into contact with said sample surface so that said measuring tip is excited to vibrations oriented lateral to said sample surface and perpendicular to said longitudinal extension of said cantilever, torsional vibrations being induced in said cantilever which are detected and analyzed by an evaluation unit, said vibration excitation causing oscillations of said measuring tip including harmonic vibrations relative to the excitation frequency and said vibration excitation includes excitation amplitudes which cause torsional amplitudes within the cantilever with maximum values thereof forming a plateau of resonance spectra despite increasing excitation amplitudes and the resonance spectra which undergoes, in a range of said maximum values of said torsional amplitudes, a widening which is determinable by a plateau width, comprising:
using at least one of the plateau of said resonance spectra, a width of the plateau of said resonance spectra and/or a gradient of said resonance spectra for examining said sample surface.

2. The method according to claim 1, wherein:
sequential scanning at a multiplicity of different points of contact between said measuring tip and said sample surface successive resonance spectra are detected and analyzed.

3. The method according to claim 2, wherein:
information obtainable from said resonance curve at each point of contact between said measuring tip and said sample surface comprises at least one of a half-width value $\Delta f_r$ of said resonance curve at $f_r$ wherein $f_r$ is the excitation frequency, a plateau width, a plateau value, a gradient at said plateau or a vibration amplitude of harmonics are recorded and represented as encoded color values.

4. The method according to claim 1, wherein:
tribological properties are analyzed and qualitatively and/or quantitatively determined.

5. The method according to claim 4, wherein:
the tribological properties comprise a frictional force and/or frictional coefficients at said sample surface.

6. The method according to one of the claim 1, wherein:
said measuring tip makes contact on said sample surface with a vertical load which is constantly adjusted by said means for driving.

7. The method according to claim 1, wherein:
said ultrasound generator emits a continuous wave signal vibrating at said excitation frequency with said continuous wave signal being varied by means of frequency wobbulation within a given excitation frequency range.

8. The method according to claim 7, wherein:
said excitation frequency range is selected such that the resonant vibration of said cantilever in contact with said sample surface via said measuring tip is contained within said frequency range.

9. The method according to claim 8, wherein:
said sample surface is impinged with a frequency sweep for determining the resonant vibration of said cantilever lying on said sample surface with said measuring tip.

10. The method according to claim 9, wherein:
said frequency sweep comprises the following range of frequencies f:

$f < f_r$ and $f < 30 f_r$.

where fr is a resonant frequency.

11. The method according to claim 7, wherein:
said excitation frequency range comprises frequencies ranging from $f_r - \frac{1}{2} f_r$ to $f_r + \frac{1}{2} f_r$, corresponding to a half-width value of a resonance curve at $f_r$.

12. The method according to claim 11, wherein:
said frequency range comprises $f_r - \frac{1}{2}\Delta f_r$ to $f_r + \frac{1}{2}\Delta f_r$, with $\Delta f_r$ corresponding to a half-width value of the resonance curve at $f_r$.

13. The method according to claim 7, wherein:
said torsional vibrations of said cantilever lying on said sample surface with said measuring tip are detected using said sensor unit at a frequency range n $\Delta f_a$, with n<25, wherein $\Delta f_a$ is the excitation frequency range.

14. The method according to claim 13 wherein $2 \leq n \leq 10$.

15. The method according to claim 1, wherein:
said vibration excitation of said sample surface is caused by said ultrasound generator so that said ultrasound generator is directly or indirectly acoustically connected with said sample surface.

16. The method according to claim 1, wherein:
a microscopic image of said sample surface is obtained by means of sequentially scanning said sample surface which said microscopic image containing information relating to a surface topography and tribological properties.

17. The method according to claim 1, wherein:
said torsional vibrations inside said cantilever are detected by said sensor unit and sensor signals obtained by said sensor unit are examined with a wideband amplifier followed by spectral analysis.

18. The method according to claim 17, wherein:
said spectral analysis is conducted using numerical Fourier transformation or FFT, Wavelet-transformation or Walsh-transformation.

* * * * *